United States Patent [19]

Archibald et al.

[11] Patent Number: 5,064,842
[45] Date of Patent: Nov. 12, 1991

[54] 1,4-DIHYDROPYRIDINES

[75] Inventors: John L. Archibald, Farnham Royal; Terence J. Ward; Albert Opalko, both of Maidenhead, all of England

[73] Assignee: John Wyeth & Brother Limited, Maidenhead, England

[21] Appl. No.: 544,097

[22] Filed: Jun. 25, 1990

Related U.S. Application Data

[63] Continuation of Ser. No. 309,018, Feb. 7, 1989, abandoned, which is a continuation of Ser. No. 7,684, Jan. 28, 1987, abandoned.

[30] Foreign Application Priority Data

Feb. 3, 1986 [GB] United Kingdom ............... 8602518

[51] Int. Cl.$^5$ .................... A61K 31/44; C07D 405/06
[52] U.S. Cl. .................... 514/341; 546/278; 546/256; 546/261; 546/264; 546/266; 546/255; 546/271; 546/277; 546/118; 546/159; 546/167; 546/141; 546/143; 546/148; 514/303; 514/307; 514/309; 514/310; 514/314; 514/338; 514/342; 514/343; 514/332; 514/333; 514/334
[58] Field of Search ............... 546/278, 256, 261, 264, 546/266, 255, 271, 277, 118, 159, 167, 141, 143, 148; 514/303, 307, 341, 309, 310, 314, 338, 342, 343, 332, 333, 334

[56] References Cited

U.S. PATENT DOCUMENTS 4,607,041 8/1986 Baxter et al. ..................... 546/321

FOREIGN PATENT DOCUMENTS 88274 9/1983 European Pat. Off. .
100189 2/1984 European Pat. Off. .

OTHER PUBLICATIONS

Merk Index 9th edition pp. 1047–1048.

Primary Examiner—Jane T. Fan
Attorney, Agent, or Firm—Arthur G. Seifert

[57] ABSTRACT

The invention concerns compounds of formula

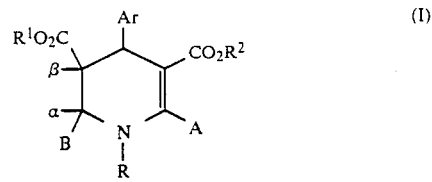

or salts thereof;

wherein:

$\alpha$ and $\beta$ together represent a bond and additionally when B is an electron withdrawing group $\alpha$ can also represent OH and $\beta$ can represent hydrogen;

Ar is an optionally substituted aryl or heteroaryl radical;

R represents hydrogen or an optionally substituted alkyl or aralkyl group;

$R^1$ and $R^2$ are the same or different and are selected from hydrogen and saturated or unsaturated, cyclic or acyclic aliphatic hydrocarbon residues optionally substituted by one or more groups selected from halogen, OH, carboxy, CN, alkoxy, alkylthio, aryloxy, alkoxycarbonyl, amino, substituted amino, and optioanlly substituted aryl or heteroaryl;

A represents a group of formula —$XR^3$ wherein X is a group of formula —$(CHR^6)_p$—Y—$(CHR^7)_q$— in which formula: Y represents —O—, —S—, $NR^8$ or a direct bond, p and q each represent 0, 1 or 2 $R^6$, $R^7$ and $R^8$ independently represent hydrogen or lower alkyl and $R^3$ is an optionally substituted nitrogen ring heteroaryl radical optionally containing other ring heteroatoms selected from oxygen, nitrogen or sulphur; B represents haloalkyl, optionally substituted phenyl, —CN, —CHO, —CH(Oloweralkyl)$_2$ or —CH$_2$OH.

36 Claims, No Drawings

1,4-DIHYDROPYRIDINES

This application is a continuation of application Ser. No. 07/309,018, filed Feb. 7, 1989, which is a continuation of Ser. No. 07/007,684, filed Jan. 28, 1987, now both abandoned.

This invention relates to heterocyclic compounds possessing pharmaceutical activity, more particularly to 1,4-dihydropyridines, processes for preparing them and pharmaceutical compositions containing them.

In one aspect this invention provides a compound of formula

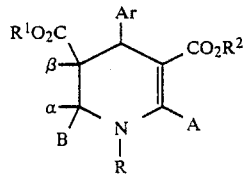

or a salt thereof;
wherein:
α and β together represent a bond and additionally when B is an electron withdrawing group α can also represent —OH and β can represent hydrogen,
Ar is an optionally substituted aryl radical;
R represents hydrogen or an optionally substituted alkyl or aralkyl group;
$R^1$ and $R^2$ are the same or different and are selected from hydrogen and saturated or unsaturated, cyclic or acyclic aliphatic hydrocarbon residues optionally substituted by one or more groups selected from halogen, OH, carboxy, CN, alkoxy, alkylthio, aryloxy, alkoxycarbonyl, amino, substituted amino, and optionally substituted aryl;
A represents a group of formula —$XR^3$ wherein X is a group of formula —$(CHR^6)_p$—Y—$(CHR^7)_q$— in which formulae: Y represents O, —S—, $NR^8$ or a direct bond, p and q each represent 0, 1 or 2; $R^6$, $R^7$ and $R^8$ independently represent hydrogen or lower alkyl, and $R^3$ is an optionally substituted nitrogen ring heteroaryl radical optionally containing other ring heteroatoms selected from oxygen, nitrogen or sulphur, B represents haloalkyl, optionally substituted phenyl, —CN, —CHO, —CH(O lower alkyl)$_2$ or —CH$_2$OH.

By the term aryl when used as a group or part of a group (e.g. aryloxy, arylalkyl) is meant any monovalent carbocyclic or heterocyclic radical possessing aromatic character and includes groups having 5 to 10 ring atoms such as phenyl, naphthyl, pyridyl (e.g. 2-, 3- or 4-pyridyl), thienyl (e.g. 2-thienyl) furyl (e.g. 2-furyl), quinolyl (e.g. 2-, 3- or 4-quinolyl), isoquinolyl (e.g. 2,3- or 4-isoquinolyl) and benzimidazolyl. Preferred heteroatoms are nitrogen, oxygen and sulphur. Examples of heterocyclic aromatic rings containing two heteroatoms are imidazolyl, e.g. 1-imidazolyl, thiazolyl e.g. 5-thiazolyl and pyrimidyl e.g. 5-pyrimidyl.

The term alkyl when used to signify a group or part of a group such as arylalkyl or alkyloxy means any straight or branched saturated aliphatic hydrocarbon especially those having 1 to 6 carbon atoms, e.g. 1–4 carbon atoms, or cyclic saturated aliphatic hydrocarbons especially those of 5 to 7 carbon atoms. Examples are methyl, ethyl, n-propyl, isopropyl, n-butyl, n-hexyl and cyclohexyl.

By the term 'optionally substituted' is meant optional substitution on carbon atoms by one or more substituents, e.g. substituents commonly used in pharmaceutical chemistry, e.g. halogen (e.g. Cl,Br,F), alkyl, alkyloxy, haloalkyl (e.g. $CF_3$), or haloalkoxy (e.g. $CHF_2O$—, $CF_3CH_2O$—), $NO_2$, $NH_2$, CN, alkylamino, dialkylamino, carboxy, alkyloxycarbonyl, acyl, acylamino, aryl (e.g. phenyl) or aminoalkyl.

Examples of the group R are groups as described above in connection with alkyl, aryl and arylalkyl and include hydrogen, methyl, ethyl, n-propyl, isopropyl and benzyl. Preferably R is hydrogen.

The groups $R^1$ and $R^2$ can be independently hydrogen, or saturated or unsaturated acylic hydrocarbon chains of 1 to 6 carbon atoms, e.g. lower alkyl or alkenyl, optionally substituted by aryl of 5 to 10 ring atoms, lower alkoxy, amino, diloweralkylamino, carboxyl or lower alkoxycarbonyl.

Examples of $R^1$ and/or $R^2$ are methyl, ethyl, n-propyl, isopropyl, butyl, methoxymethyl, methoxyethyl, ethoxymethyl, ethoxyethyl, methoxypropyl, aminomethyl, 2-aminoethyl, 3-aminopropyl, dimethylaminoethyl, 2-carboxyethyl, ethoxycarbonylmethyl. When $R^1$ or $R^2$ is alkyl substituted by optionally substituted aryl (including heteroaryl) examples are benzyl, pyridylmethyl or -ethyl (e.g. 3-pyridylmethyl), imidazolylmethyl (e.g. 1-imidazolylmethyl) or imidazolylethyl.

Preferred values for $R^1$ and/or $R^2$ are methyl and ethyl.

$R^3$ can be a mono- or bi-cyclic nitrogen ring heteroaryl radical containing 5 to 10 ring atoms.

Examples of $R^3$ are imidazolyl (e.g. 1-or 3-imidazolyl), pyridyl (e.g. 2-or 3-pyridyl), thiazolyl (e.g. 2-thiazolyl), pyrrolyl (e.g. 1-pyrrolyl) or bicyclic rings such as benzimidazolyl (e.g. 1-benzimidazolyl), quinolyl (e.g. 2- or 4-quinolyl), isoquinolyl (e.g. 1- or 4-isoquinolyl), imidazopyridyl (e.g. 5-imidazo[1,5-a]-pyridyl). Preferred values are 1-imidazolyl, 3-pyridyl and 5-imidazo[1,5-a]-pyridyl.

Examples of X are independently —NH; —O—; —S—; —$CH_2$—; —$CH(CH_3)$—; —$OCH_2$—; —$CH_2$—; —$(CH_2)_2$—O—; —$CH_2CH(CH_3)$—; $CH(CH_3)CH_2$—; or a group of formula —$CH_2$—Z—$CH_2$—, —$CH_2$—Z—$(CH_2)_2$—, —$(CH_2)_2$—Z—$CH_2$—where Z is S, NH or a direct bond.

Examples of B are—CN,—CHO,—$CH_2(OMe)_2$ or alkyl groups of 1 to 3 carbon atoms substituted by one or more halogen atoms such as fluorine, chlorine and/or bromine especially mono-, di or tri-fluoromethyl, mono, di- or tri-chloromethyl.

Preferred examples of X are —$CH_2$—, —$(CH_2)_2$—, —$CH(CH_3)$—, —$CH_2CH(CH_3)$—, —$CH(CH_3)CH_2$—, —$CH_2O$—, —$CH_2NH$—and —$CH_2$—S—. Preferably B is —$CH_2F$.

Examples of Ar are groups mentioned above for the definitions of aryl and included in the preferred values are 2- and/or 3-substituted phenyl groups, e.g. 2- and/or 3-nitrophenyl; 2,3-dichlorophenyl; 2-trifluoromethylphenyl, pentafluorophenyl, naphthyl (e.g. 1-naphthyl), pyridyl (e.g. 2-pyridyl), halopyridyl (e.g. 2-chloropyrid-3-yl), benzimidazolyl (e.g. 4- or 7-benzimidazolyl).

Particularly preferred compounds provided by this invention have formula Ia:

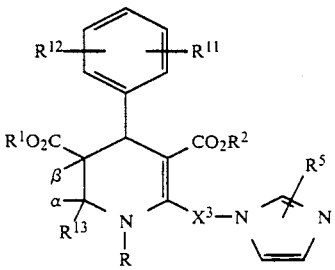

wherein α, β, R, R¹ and R² have the meanings given above, $R^5$ is H or lower alkyl, $X^3$ is —$CH_2$—, —$CH_2NHCH_2$—, —$CH_2NH(CH_2)_2$—, —$CH_2CH_2$—, —$(CH_2)_2O$, or —$CH_2O$—, —$CH(CH_3)$—; $R^{11}$ and $R^{12}$ are each selected from hydrogen, nitro, halo or trifluoromethyl and $R^{13}$ is CN, chloro- or fluoro-alkyl especially —$CH_2F$, $CHF_2$, $CF_3$ or —$CH_2Cl$ or a salt thereof, or an optically active isomer thereof.

In formula Ia preferably R is hydrogen.

Examples of $R^1$ are H, Me, Et $^n$Pr or $^i$Pr. Examples of $R^2$ are Me and Et. When $R^{11}$ is hydrogen examples of $R^{12}$ are 3-nitro, 2-trifluoromethyl. Examples of $R^{11}$ and $R^{12}$ when substituents are 2,3-dihalo, e.g. are 2,3-dichloro, 3-nitro-2-halo and 3-halo-2-nitro.

The term "lower" as used herein denotes 1 to 6 carbon atoms.

Other preferred compounds are compounds of formula Ia in which 1-imidazolyl is replaced by a pyridine ring, preferably pyrid-3-yl.

In the compounds of the invention α and β together preferably represent a bond.

The compounds of formula I possess pharmaceutical activity in particular antihypertensive and/or hypotensive activity when tested on warm blooded animals and hence are indicated for the treatment of high blood pressure. In addition since the compounds of this invention antagonise calcium movement into the cell they are also vasodilators and useful in the treatment of a variety of cardiac conditions such as heart attacks, angina pectoris, cardiac arrythmias, cardiac hypertrophy and coronary vasospasm. Furthermore the compounds of formula I also inhibit blood platelet aggregation and inhibit thromboxane synthetase. These latter activities in combination with their antihypertensive properties makes these compounds potentially very useful for the treatment of cardiovascular disorders, especially thrombosis.

Antihypertensive activity is demonstrated by the following standard procedure:

The blood pressures of male or female spontaneously hypertensive rats are measured in a 37° C. constant temperature housing by means of a tail cuff. Rats with systolic pressures below 155 mmHg are discarded. Groups of rats are dosed orally with the test substance in a suitable vehicle or with vehicle alone. Systolic pressures are recorded before dosing and at selected time points afterwards. Heart rates are derived from caudal artery pulses. Results are analysed statistically by means of 2 way analysis of variance (within group).

Calcium antagonist activity is demonstrated by examining drug effect on the response of isolated rat portal vein to increasing calcium ion concentration in vitro.

Ability to inhibit blood platelet aggregation is tested for by a modification of the procedure of Fantl, Australian J.Exp.Biol.Med.Sci. 45, 355–62 1967.

Since platelet aggregation is the initial step in thrombus formation it is considered that compounds which prevent aggregation or reduce platelet adhesiveness may inhibit the initiation of the atherosclerotic process. The effect of drugs on adhesiveness is measured in platelet-rich plasma containing a small amount of arachidonic acid which markedly increases aggregation in vitro and may be a physiological agent for doing so in vivo. The actual test procedure used is described below.

New Zealand White rabbits (2.5–3 kg) are anaesthetised with an injection, via the marginal ear vein, of sodium pentobarbitone 30–40 mg/kg. The carotid artery is cannulated and blood (100–150 ml) is withdrawn into 50 ml syringes containing 3.8% sodium citrate (Ratio blood: citrate=9:1).

Blood is centrifuged at 200 g (1500 r.p.m.) for 10 minutes at 5° C. and the platelet rich plasma (PRP) removed. The platelets are then kept at room temperature in a screw topped plastic centrifuge tube for the duration of the experiment.

A twin channel platelet aggregometer—(HU aggregometer, A.Browne Ltd, Leicester, UK) is used. 1.0 ml aliquots of PRP are prewarmed for 5–10 minutes and stirred continuously at 1100 rpm. Aggregation is induced by addition of 250 μM arachidonic acid, (8 μl volume) to the PRP samples. The aggregometer output is set at maximum and the chart recorder sensitivity is altered to give a full scale deflection to this arachidonic acid response.

Control responses are recorded as the maximum deflection obtained after addition of 250 μM arachidonic acid.

PRP samples are preincubated for 5 minutes with the test compounds followed by arachidonic acid addition. The maximum deflection after the addition of arachidonic acid is then recorded. All drugs are screened initially at $10^{-4}$M (final concentration), i.e. 10 μl of a $1 \times 10^{-2}$M stock solution of the drug dissolved in distilled water is added to the PRP.

Dazoxiben, a thromboxane synthetase inhibitor (Randall, M.J. et al Research 23 145–162, 1981) is used as a positive control and all test components are compared with Dazoxiben.

Compounds possessing thromboxane synthetase inhibitory activity are useful in the treatment or prevention of diseases responsive to the inhibition of thromboxane synthetase especially cardiovascular disorders such as thrombosis, atherosclerosis, cerebral ischaemic attacks; and angina pectoris; peripheral vascular diseases and migraine.

The ability to inhibit thromboxane production is demonstrated by the following standard test:

a) Generation of thromboxanes

Blood (approx. 75 ml) is obtained from an anaesthetised rabbit and centrifuged at 200 g for 10 minutes to obtain platelet rich plasma (PRP). An aliquot of PRP is incubated for 10 minutes at 37° C. in the presence of vehicle or drug. Platelet aggregation is induced by the addition of adenosine diphosphate and adrenaline. The tubes are incubated for 3 minutes, centrifuged at 10,000 g for 3 minutes and a 50 ml aliquot of the supernatant taken for radio-immunoassay of thromboxane $B_2$ ($TxB_2$).

b) Radio-immunoassay of $TxB_2$

The total incubation volume is 150 $\mu$l containing 50 $\mu$l of $^3H$—$TxB_2$ (0.005 $\mu$Ci), 50 $\mu$l of sample or authentic $TxB_2$ ranging from 5 to 300 pg per tube as standards and 50 $\mu$l of rabbit anti-sera to $TxB_2$ (in a concentration which will bind 50% of H-$TxB_2$). After incubation for 1 hour at room temperature the tubes are further incubated for 16-20 hours at 4° C. 1 ml of dextran-coated charcoal (2.5% w/v suspension in phosphate buffer pH 7.4) is then added to the tubes which are further incubated on ice for 10 minutes. Following the incubation the samples are 5 centrifuged at 10,000 g for 10 minutes and 500 $\mu$l of the supernatant added to 5 ml of scintillation cocktail. Measurement of the radioactivity in the supernatant quantifies the amount of $[^3H]$—$TxB_2$ bound by the antibody. The concentration of unlabelled $TxB_2$ in the sample is then determined from a linear standard curve.

This invention also provides processes for preparing the compounds of formula I. In general both the compounds of formula I and intermediates of analogous structure may be prepared by processes which are known or are analogous to known processes; see for example Drugs of the Future, Vol. VI, No. 7, 1981 pps 427-440. A first general process for preparing compounds of formula I as hereinbefore defined wherein B is fluoroalkyl, —CN, —CHO, —$CH_2OH$,—CH(O lower alkyl)$_2$ or optionally substituted phenyl with the proviso (a) that when Y is O, —S—or —$NR^8$—then p is 1 or 2, comprises reacting corresponding compounds of formula

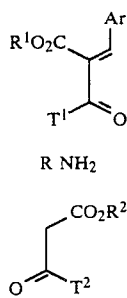

II

R $NH_2$     III

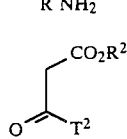

IV wherein Ar, R, $R^1$ and $R^2$ are as defined above, and one of $T^1$ and $T^2$ is A, the other is B wherein A and B are as defined immediately above. The process is conveniently carried out by heating, e.g. at reflux, in an inert solvent preferably polar such as ethanol, toluene, dimethylformamide, isopropanol, acetonitrile.

A second general process for preparing compounds of formula I as hereinbefore defined and subject to the proviso (a) in the first process mentioned above, comprises reacting a corresponding compound of formula II as shown above with a corresponding compound of formula

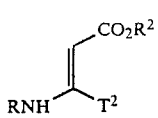

(V)

wherein Ar, R, $R^1$ and $R^2$ are as defined above, and one of $T^1$ and $T^2$ is A, the other is B. This process may conveniently be carried out by heating e.g. at reflux in an inert solvent (preferably polar) such as ethanol, acetonitrile, isopropanol, toluene or dimethylformamide.

In yet a further process compounds of formula I wherein the proviso (a) above applies may be prepared by reacting a compound of formula ArCHO with corresponding compounds of formula VI and V shown below

and

wherein Ar, R, $R^1$ and $R^2$ are as defined above and one of $T^1$ and $T^2$ is A, the other is B. Such a process may be carried out by heating the reactants, e.g. at reflux, in an inert solvent (preferably polar) such as ethanol, acetonitrile, isopropranol, toluene or dimethylformamide.

In the aforementioned processes when B is an electron withdrawing group compounds of formula I can be prepared wherein $\alpha$ and $\beta$ are a) a bond or b) $\alpha$ is hydroxy and $\beta$ is hydrogen. If dehydrating conditions e.g. high reaction temperatures are simultaneously employed then the process favours the production of a 1,4-dihydropyridine product.

Compounds of formula I may be prepared by reacting compounds of formula

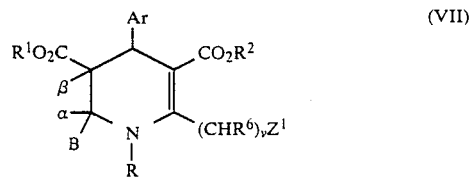

and

in which formulae B is fluoroalkyl, CN, CHO, $CH_2OH$, CH(O lower alkyl)2 or optionally substituted phenyl; $\alpha$, $\beta$, R, $R^1R^2$, $R^3$, $R^6$ and $R^7$ are as defined above, one of $Z^1$ and $Z^2$ is halogen (other than fluorine when B is fluoroalkyl) or a sulphonyloxy group; the other of $Z^1$ and $Z^2$ is —YH or $Y^-$ as appropriate (wherein Y is as defined above) and v and w are each 0, 1 or 2 with the proviso that (i) when v is 2 and $Z^2$ is YH or $Y^-$ then $Z^1$ can also represent dialkylamino, e.g. —$NMe_2$ or a quaternary ammonium group, e.g. —$NMe_3^+$ $I^-$.

The reaction may be carried out in an inert solvent in the presence of base, e.g. $K_2CO_3$ or a tertiary amine, e.g. triethylamine. Anions of the requisite starting materials may be generated by the usual methods known in the art and reacted. Examples of sulphonyloxy are alkyl or aralkyl- or aryl-sulphonyloxy, e.g. tosyloxy or mesyloxy. When $\alpha$ is OH and/or $\beta$ is —$CH_2OH$, the hydroxy group(s) may be protected e.g. as a benzyl ether before the reaction and deprotected afterwards.

The starting materials of formula VII wherein $Z^1$ is halogen, sulphonyloxy as defined above may be prepared by known methods, e.g. from corresponding compounds of formula

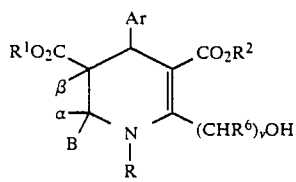
(IX)

by methods known for the conversion of OH to halogen or sulphonyloxy. Compounds of formula IX wherein v=0 may be prepared by reacting a compound of formula X

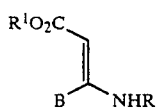
(X)

wherein R, $R^1$ and B are as hereinbefore defined with compounds of formulae

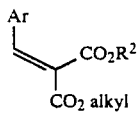
(XI)

in which formula Ar and $R^2$ are as defined above.

Compounds of formula IX wherein V is 1 or 2 may be prepared by reacting a compound of formula

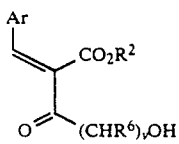

wherein v is 1 or 2 and Ar and $R^2$ are as defined above with a compound of formula (X) as hereinbefore defined.

Compounds of formula VII wherein v is 1, $R^6$ is hydrogen and $Z^1$ is chlorine or bromine may also be prepared by halogenating a corresponding compound of formula

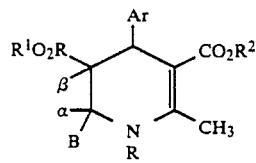
(XIII)

wherein Ar, R, $R^1$, $R^2$, $\alpha$ and $\beta$ are as defined above, e.g. using phenyl trimethylammonium tribromide. Compounds having formula XII are disclosed in EP Publication No. 125803A.

Compounds of formula VII wherein v is 2 and $Z^1$ is —N(alkyl)$_2$ or a quaternary ammonium group may be prepared by performing a Mannich reaction on a compound of formula

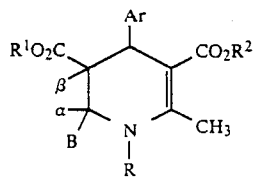
(XIII)

using formaldehyde and secondary amine and if required reacting the product with an alkyl halide. Compounds of formula VII wherein $Z^1$ is $Y^-$ may be prepared by known methods. For example, when $Z^1$ is —OH, —NHR$^8$ or —SH anions may be formed in the presence of a strong base, e.g. an alkali metal hydride such as NaH or BuLi. When Y is a direct bond carbanions may be prepared from the corresponding halo compound using for example, lithium diisopropylamine or BuLi.

Compounds of formula I wherein $\alpha$ and $\beta$ are a bond may also be prepared by dehydrating a compound of formula I wherein $\alpha$ represents OH and $\beta$ represents hydrogen and Ar,A,B,R,$R^1$ and $R^2$ are as defined above. This process may be carried out in a solvent which is inert under the reaction conditions, e.g. $CH_2Cl_2$ and in the presence of a dehydrating agent, e.g. $(CF_3CO)_2O$, and a base, e.g. pyridine. The dehydration may also be effected using diethylaminosulphur trifluoride. When the latter reagent is used and B is $CH_2OH$ or CHO then these groups will be converted during the reaction to —$CH_2F$ and —$CHF_2$ respectively.

When B is —CHO in a compound of formula I selective reduction e.g. using an alkali metal borohydride in an alcoholic solvent, gives a compound of formula I wherein B is —$CH_2OH$. This reaction may be conveniently carried out using sodium borohydride in ethanol.

Compounds of formula I wherein B is —$CH_2F$ or —$CHF_2$ and $\alpha$ and $\beta$ are a bond may also be prepared by reacting a corresponding compound of formula I wherein B is —CHO or —$CH_2L$ where L is OH or a leaving group with a fluorinating agent such as a dialkylaminosulphur trifluoride, e.g. diethylaminosulphur trifluoride or (2-chloro-1,1,2-trifluoroethyl)diethylamine. Examples of L are organic sulphonyloxy groups such as alkyl, aralkyl- or aryl-sulphonyloxy, especially —$OSO_2$ lower alkyl, —$OSO_2$aryl where aryl is for example p-tolyl. The reaction may be carried out with heating in an inert solvent such as methylene dichloride.

When B is —CH(O lower alkyl)$_2$ in a compound of formula I then this group may be hydrolysed selectively to give a compound of formula I wherein B is —CHO. The hydrolysis may be carried out under aqueous acid conditions e.g. hydrochloric acid in a water miscible solvent such as acetone, with or without heating.

Compounds of formula I wherein B is CN may be prepared by removing the elements $R^{10}OH$ from a compound of formula

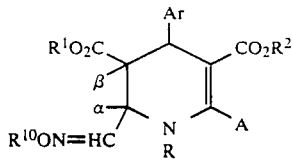
(XIV)

wherein Ar, R, $R^1$, $R^2$, A, $\alpha$ and $\beta$ are as defined above and $OR^{10}$ represents hydroxy or a leaving group, e.g. a 2,4-dinitrophenoxy group using a dehydrating agent e.g. acetic anhydride or thionyl chloride under mild conditions that will not affect other substituents in the molecule.

Compounds of formula XIV may be prepared from the corresponding formyl compound by known methods.

Compounds of formula I wherein R is other than hydrogen may be prepared by alkylating a compound of formula I wherein R is H in the presence of a strong base, e.g. an alkali metal hydride, with a compound of formula R—halogen where R is as defined above other than hydrogen.

Compounds of formula I having ester functional groups, e.g. cyanoethyl- or t-butyl-ester, may be hydrolysed, selectively if appropriate, to give compounds of formula I having carboxyl groups. Alternatively carboxyl groups can be esterified.

In any of the aforementioned reactions reactive substituent groups may be protected if susceptible to the reaction conditions and deprotected afterwards.

The compounds of formula I possess one or more asymmetric centres and hence optical isomers and mixtures thereof are possible. All such isomers and mixtures thereof are included within the scope of this invention. Where any reaction process produces mixtures of such isomers standard resolution techniques may be applied to separate a specific isomer.

In any of the aforementioned reactions compounds of formula I may be isolated in free base form or as acid addition salts as desired. Examples of such salts include salts with pharmaceutically acceptable acids such as hydrochloric, hydrobromic, hydroiodic, sulphuric, phosphoric, nitric, acetic, citric, tartaric, fumaric, succinic, malonic, formic, maleic acid or organosulphonic acids such as methane sulphonic or p-tolyl sulphonic acids.

When acidic substituents are present it is also possible to form salts with bases e.g. alkali metal (such as sodium) or ammonium salts. Such salts of the compounds of formula I are included within the scope of this invention.

When basic substituents are present then quaternary ammonium salts may be formed by quaternizing with an alkylating agent such as alkyl, or aralkyl halides.

Starting materials for the processes described herein are known compounds or can be prepared by analogous methods for known compounds.

This invention also provides pharmaceutical compositions comprising a compound of formula I or a pharmaceutically acceptable salt thereof.

For the pharmaceutical compositions any suitable carrier known in the art can be used. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet disintegrating agents; it can also be encapsulating material. In powders the carrier is a finely divided solid which is in admixture with the finely divided active ingredient. In tablets the active ingredient is mixed with a carrier having the necessary binding properties and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formulation of an active ingredient with encapsulating material as carrier, to give a capsule in which the active ingredient (with or without other carriers) is surrounded by carriers, which is thus in association with it. Similarly cachets are included.

Sterile liquid form compositions include sterile solutions, suspensions, emulsions, syrups and elixirs.

The active ingredient can be dissolved or suspended in a pharmaceutically acceptable carrier, such as sterile water, sterile organic solvent or a mixture of both. The active ingredient can often be dissolved in a suitable organic solvent, for instance aqueous propylene glycol containing from 10 to 75% of the glycol by weight is generally suitable. Other compositions can be made by dispersing the finely-divided active ingredient in aqueous starch or sodium carboxymethyl cellulose solution, or in a suitable oil, for instance arachis oil.

Preferably the pharmaceutical composition is in unit dosage form, the composition is sub-divided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in packaged form. The quantity of active ingredient in a unit dose of composition may be varied or adjusted from 10 to 500 mg or more, e.g. 25 mg to 250 mg, according to the particular need and the activity of the active ingredient. The invention also includes the compounds in the absence of carrier where the compounds are in unit dosage form. Based on the results from animal studies the dosage range for the treatment of humans using a compound of formula I will be in the range from about 5 mg to 500 mg per day depending on the activity of the compound.

The following Examples illustrate the invention and methods for preparing compounds of the invention. Since the final product may be sensitive to light, light should be excluded whenever possible during and after synthesis of compounds of the invention.

EXAMPLE 1

1,4-Dihydro-2-fluoromethyl-6-(imidazol-1-ylmethyl)-4-(3-nitrophenyl)pyridine-3,5-dicarboxylic acid 3-methyl 5-ethyl diester A mixture of methyl 3-amino-4-fluoro-2-butenoate, -nitrobenzaldehyde and ethyl 4-(imidazol-1-yl) acetoacetate in ethanol solvent is refluxed for several hours to give the title compound.

EXAMPLES 2–21

Using a procedure analogous to Example 1 according to the reaction scheme

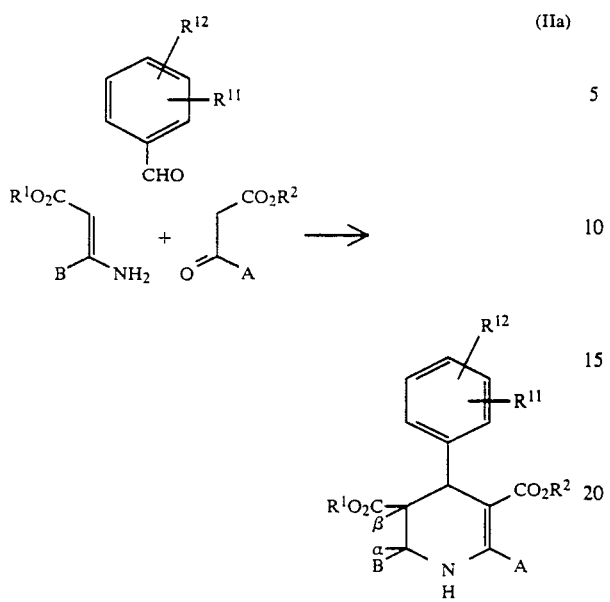

the following compounds of formula IIa are prepared:

| Ex. No. | α/β | R¹ | R² | Ar | B | A |
|---|---|---|---|---|---|---|
| 2. | bond | Me | Et | 2,3-dichlorophenyl | —CH₂F | imidazol-1-ylmethyl |
| 3. | bond | Me | Me | " | —CH₂F | imidazol-1-ylmethyl |
| 4. | " | Et | Et | 2-nitrophenyl | —CH₂F | imidazol-1-ylethyl |
| 5. | " | Me | Me | " | —CH₂F | imidazol-1-ylethyl |
| 6. | " | Me | Et | 3-nitrophenyl | —CH₂F | pyrid-3-yloxymethyl |
| 7. | " | Et | Et | " | —CH₂F | imidazol-1-ylethyl |
| 8. | " | Et | Et | 2-fluoro-5-nitro-phenyl | —CH₂F | imidazol-1-ylmethyl |
| 9. | " | Me | Me | 2-trifluoromethyl-phenyl | —CH₂F | imidazol-1-ylmethyl |
| 10. | " | Et | Et | 2-trifluoromethyl-phenyl | —CH₂F | imidazol-1-ylmethyl |
| 11. | OH/H | Me | Et | 3-nitrophenyl | —CF₃ | imidazol-1-ylmethyl |
| 12. | bond | Me | Et | " | —CHF₂ | imidazol-1-ylmethyl |
| 13. | " | ⁱPr | Et | " | —CH₂F | imidazol-1-ylmethyl |
| 14. | " | Me | Et | difluoromethoxy-phenyl | —CH₂F | imidazol-1-ylmethyl |
| 15. | " | Me | Et | benzofurazan-4-yl | —CH₂F | imidazol-1-ylmethyl |
| 16. | " | Me | Et | 3-nitrophenyl | —CH₂(OMe)₂ | imidazol-1-ylmethyl |
| 17. | " | Me | Et | 3-nitrophenyl | —CH₂(OEt)₂ | imidazol-1-ylmethyl |
| 18. | " | Me | Me | 2,3-dichlorophenyl | " | imidazol-1-ylmethyl |
| 19. | " | Me | Et | 2-trifluoromethyl-phenyl | " | imidazol-1-ylmethyl |
| 20. | " | Me | Et | benzofurazan-4-yl | —CH₂(OMe)₂ | imidazol-1-ylmethyl |
| 21. | " | Me | Et | 2-difluoromethoxy-phenyl | " | imidazol-1-ylmethyl |

EXAMPLE 22

2-Formyl-1,4-dihydro-6-(imidazolyl-1-ylmethyl)-4-(3-nitrophenyl)pyridine-3,5-dicarboxylic acid-3-methyl 5-ethyl ester (a) The compound of Example 16, 1,4-dihydro-2-(imidazol-1-ylmethyl-6-dimethoxymethyl-4-(3-nitrophenyl)-pyridine 3,5-dicarboxylic acid 3-ethyl 5-methyl diester, is treated with 2M hydrochloric acid at room temperature to give the title compound.

(b) By a similar procedure the compounds of Examples 17-21 are hydrolysed to the corresponding formyl derivatives.

EXAMPLE 23

2-Cyano-1,4-dihydro-6-(imidazol-1-ylmethyl)-4-(3-nitrophenyl)pyridine-3,5-dicarboxylic acid 3-methyl 5-ethyl ester a) 2-Formyl-1,4-dihydro-6-(imidazol-1-ylmethyl)-4-(3-nitrophenyl)pyridine-3,5-dicarboxylic acid 3-methyl 5-ethyl ester is mixed with 0-(2,4-dinitrophenyl)hydroxylamine in ethanol and 1 drop of concentrated H₂SO₄ is added to give 2-(2,4-dinitrophenoxyiminomethyl)1,4-dihydro-6-(imidazol-1-ylmethyl)-4-(3-nitrophenyl)pyridine-3,5-dicarboxylic acid 3-ethyl 5-methyl ester. Treatment of this product with KOH in ethanol solvent whilst refluxing gives the title compound.

b) By a similar procedure to Examples 22 and 23 the compounds of Examples 17 to 21 are converted to their corresponding 2-cyano derivatives.

EXAMPLE 24

1,4-Dihydro-2-hydroxymethyl-6-(imidazol-1-ylmethyl)-4-(3-nitrophenyl)pyridine-3,5-dicarboxylic acid 3-methyl 5-ethyl ester The compound of Example 22 is treated with NaBH₄ in ethanol solvent to give the title compound.

In a similar manner to Examples 22 and 24 the compound of Examples 17 to 21 are converted to their corresponding 2-hydroxymethyl derivatives.

EXAMPLE 25

2-Trifluoromethyl-1,4-dihydro-6-(imidazol-1-ylmethyl)-4-(3-nitrophenyl)pyridine-3,5-dicarboxylic acid 3-methyl 5-ethyl ester The compound of Example 11 is dehydrated using 1:1 v/v pyridine and trifluoroacetic anhydride to give the title compound, m.p. 190°-190.5° C. (hydrochloride).

EXAMPLE 26

2-Fluoromethyl-1,4-dihydro-6-imidazol-1-ylmethyl)-4-(3-nitropheny)pyridine-3,5-dicarboxylic acid 5-ethyl-3-methyl ester a) 2-(Fluoromethyl)-1,4-dihydro-6-methyl-4-(3-nitrophenyl)pyridine-3,5-dicarboxylic acid 5-ethyl-3-methyl ester (prepared according to EP Publication No. 0125803A. Example 8; 3.62 g, 10 mmol) in dichloromethane (40 ml) was treated portion wise with phenyltrimethylammonium tribromide (3.76 g, 10 mmol) over 5 minutes at room temperature. After 1 hour the mixture was shaken with water (50 ml, then 2×25 ml), then with saturated (brine (25 ml), dried (NaSO$_4$) and evaporated, leaving the impure bromo compound (2-bromomethyl-6-fluoromethyl-1,4-dihydro-4-(3-nitrophenyl)pyridine 3,5-dicarboxylic acid 3-ethyl 5-methyl diester) as a yellow foam (4.47 g).

b) The crude bromo compound (4.47 g) was dissolved in THF and poured into a solution of imidazole (6.8 g, 0.1 mole, 10 equiv.) in THF (total volume 40 ml). The solution was kept at room temperature for 67 hours and was then concentrated to a yellow oil which was treated with 2N hydrochloric acid (60 ml). The acid and residual insoluble gum mixture was extracted with ether (2×30 ml, extracts discarded) and then with chloroform (5×50 ml). The chloroform extracts were washed with water (25 ml), saturated brine (25 ml), dried (Na$_2$SO$_4$), and evaporated to a foam (3.917 g) which crystallised from propan-2-ol (40 ml) giving the title compound as fine yellow crystals (1 553 g), m.p. 199°–200° (decomp).

EXAMPLE 27

2-Trifluoromethyl-1,4-dihydro-6-(imidazol-1-ylmethyl)-4-(3-nitrophenyl)pyridine-3,5-dicarboxylic acid diethyl ester A solution of 1,4-dihydro-2-methyl-4-(3-nitrophenyl)-6-trifluoromethylpyridine-3,5-dicarboxylic acid diethyl ester (prepared according to Example 82 of EP Publication No. 125803A) (3.21 g, 7.5 mmol) in THF (15 ml) was treated at room temperature with phenyl trimethylammonium tribromide (2.82 g, 7.5 mmol) in portions over 15 minutes. The mixture 10 was stirred at room temperature for 1½ hours and then filtered into a warm solution of imidazole (5.216 g, 76.7 mmol, 10.23 equiv) in THF (151 ml). The resulting solid was washed with further THF (2×2.5 ml), adding the washings to the filtrate and the mixture was allowed to cool over 2½hours. TLC indicated complete conversion after 1 hour.

The solution was concentrated to an oil which was partitioned between ether (50 ml) and 2N hydrochloric acid (2×37.5 ml, then 15 ml). The acid phases (including a heavy oil that separated below the acid phase in the first extraction) were combined and washed with further ether (25 ml), causing the crystallisation of a solid (A) which was collected and washed with ether (20 ml). The ether phases were discarded and the filtered acid phases were extracted with chloroform (3×25 ml). The combined extracts were dried (Na$_2$SO$_4$) and evaporated, leaving a solid (B; 0.448 g).

Solids A and B were combined, dissolved in ethyl acetate (80 ml), and washed with 10% w/v aqueous potassium carbonate (2×25 ml), saturated brine (2×25 ml), dried (Na$_2$SO$_4$), and evaporated giving the title base as a gum which crystallised on trituration with ether (3.284 g).

This solid was redissolved in ethyl acetate (30 ml) and treated with excess ethereal hydrogen chloride. A solid crystallised slowly. The supernatant was decanted and the solid was recrystallised from ethyl acetate-methanol giving the hydrochloride salt of the title compound (2.583 g, mp. 190°–190.5°.

Found: C, 49.8; H, 4.4; N, 10.8; $C_{22}H_{21}F_3N_4O_6 \cdot HCl$ requires C, 49.8; H, 4.2; N, 10.55%.

We claim:

1. A compound of the formula

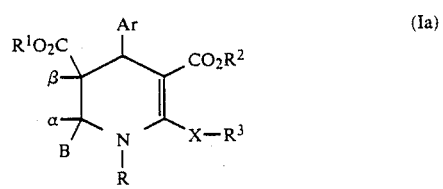

(Ia)

or a pharmaceutically acceptable salt thereof, wherein
α and β together are a bond and additionally, when B is an electron withdrawing group, α is —OH and β is —H;

Ar is phenyl, pyridyl, quinolyl or benzimidazolyl, optionally substituted by one or two substituents independently selected from halogen, lower alkyl, lower alkoxy, haloloweralkyl, haloloweralkoxy, —NO$_2$, —NH$_2$, —CN, loweralkylamino, diloweralkylamino, carboxy, loweralkyloxycarbonyl, acyl of 2 to 7 carbon atoms, or acylamino of 2 to 7 carbon atoms, or pentafluorophenyl;

R is hydrogen, methyl, ethyl, n-propyl, isopropyl, benzyl, carbmethoxymethyl or carbmethoxymethyl;

$R^1$ and $R^2$ are independently selected from hydrogen, methyl, ethyl, n-propyl, isopropyl, butyl, methoxymethyl, ethoxymethyl, methoxypropyl, aminoethyl, 2-aminoethyl, 3-aminopropyl, dimethylaminoethyl, 2-carboxyethyl, methoxycarbonylmethyl, ethoxycarbonylethyl, benzyl, 2-phenethyl, pyridylmethyl, pridylethyl, imidazolylmethyl or imidazolylethyl;

B is —CN, —CH$_2$F, —CHF$_2$, CF$_3$, or —CH$_2$Cl;
X is —NH—, —O—, —S—, —CH$_2$, —CH(CH$_3$)—, —CH(CH$_3$)CH$_2$—, —CH$_2$CH(CH$_3$)—, —OCH$_2$—, —CH$_2$O—, —(CH$_2$)$_2$—O—, —CH$_2$CH$_2$—, —CH$_2$CH$_2$CH$_2$—, —CH$_2$S—, —CH$_2$SCH$_2$—, —CH$_2$CH$_2$SCH$_2$—, CH$_2$SCH$_2$CH$_2$—, —CH$_2$NH—, —CH$_2$NHCH$_2$—, —CH$_2$NHCH$_2$—, —CH$_2$CH$_2$NHCH$_2$—, or —CH$_2$NHCH$_2$CH$_2$—;

$R^3$ is imidazolyl, pyridyl, thiazolyl, pyrrolyl, benzimidazolyl, quinolyl, isoquinolyl or imidazopyridyl, in which the term lower in reference to alkyl groups refers to such groups having 1 to 6 carbon atoms.

2. A compound of claim 1 wherein Ar is 2- or 3-nitrophenyl, 2,3-dichlorophenyl, 2-trifluormethylphenyl, pentafluorophenyl, pyridyl or halopyridyl.

3. A compound of claim 1 wherein R is hydrogen, methyl, ethyl, n-propyl, isopropyl, or benzyl.

4. A compound of claim 1 wherein R is hydrogen.

5. A compound of claim 1 wherein $R^1$ is hydrogen, methyl, ethyl, n-propyl or i-propyl and $R^2$ is methyl or ethyl.

6. A compound of claim 1 wherein $R^1$ and $R^2$ are independently methyl or ethyl.

7. A compound of claim 1 wherein B is —CH$_2$F, —CHF$_2$, CF$_3$, or —CH$_2$Cl.

8. A compound of claim 1 wherein X is —CH$_2$, —CH(CH$_3$)—, —CH(CH$_3$)CH$_2$——CH$_2$CH(32)—, —CH$_2$O—, —(CH$_2$)$_2$—O—, —CH$_2$CH$_2$—, —CH$_2$CH$_2$CH$_2$—, —CH$_2$S—, —CH$_2$NH—, —CH$_2$NHCH$_2$—, or —CH$_2$NHCH$_2$CH$_2$—.

9. A compound of claim 1 wherein R$^3$ is imidazolyl or pyridyl.

10. A compound of claim 1 wherein R$^3$ is 1-imidazolyl or pyridyl-3-yl.

11. A compound of claim 1 which is 2-trifluoromethyl-1,4-dihydro-6-(imidazol-1-ylmethyl)-4-(3-nitrophenyl)pyridine-3,5-dicarboboxylic acid diethyl ester or a pharmaceutically acceptable salt thereof.

12. A compound of claim 1 which is 2-fluoromethyl-1,4-dihydro-6-(imidazol-1-ylmethyl)-4-(3-nitrophenyl)pyridine-3,5-carboboxylic acid 5-ethyl 3-methyl ester or a pharmaceutically acceptable salt thereof.

13. A method of inhibiting thromboxane synthetase in a mammal in need thereof, comprising administering to such mammal an amount effective to inhibit thromboxane synthetase of a compound of the formula $$\begin{array}{c} \text{Ar} \\ R^1O_2C \diagup\!\!\!\diagdown CO_2R^2 \\ \beta\text{—}\diagup \quad \diagdown \\ \alpha\text{—}\diagup \quad \diagdown X\text{—}R^3 \\ B \quad N \\ \quad | \\ \quad R \end{array} \quad \text{(Ia)}$$

or a pharmaceutically acceptable salt thereof, wherein
α and β together are a bond and additionally, when B is an electron withdrawing group, α is —OH and β is —H;

Ar is phenyl, pyridyl, quinolyl or benzimidazolyl, optionally substituted by one or two substituents independently selected from halogen, lower alkyl, lower alkoxy, haloloweralkyl, haloloweralkoxy, —NO$_2$, —NH$_2$, —CN, loweralkylamino, diloweralkylamino, carboxy, loweralkyloxycarbonyl, acyl or 2 to 7 carbon atoms, or acylamino of 2 to 7 carbon atoms, or pentafluorophenyl;

R is hydrogen, methyl, ethyl, n-propyl, isopropyl or benzyl;

R$^1$ and R$^2$ are independently selected from hydrogen, methyl, ethyl, n-propyl, isopropyl, butyl, methoxymethyl, ethoxymethyl, methoxypropyl, aminoethyl, 2-aminoethyl, 3-aminopropyl, dimethylaminoethyl, 2-carboxyethyl, methoxycarbonylmethyl, ethoxycarbonylethyl, benzyl, 2-phenethyl, pyridylmethyl, pridylethyl, imidazolylmethyl or imidazolylethyl;

B is —CN, —CH$_2$F, —CHF$_2$, CF$_3$, OR —CH$_2$Cl;

X is —NH—, —O—, —S—, —CH$_2$, —CH(CH$_3$)—, —CH(CH$_3$)CH$_2$—, —CH$_2$CH(CH$_3$)—, —OCH$_2$—, —CH$_2$O—, —(CH$_2$)$_2$—O—, —CH$_2$CH$_2$—, —CH$_2$CH$_2$CH$_2$—, —CH$_2$S, —CH$_2$SCH$_2$—, —CH$_2$CH$_2$SCH$_2$—, CH$_2$SCH$_2$CH$_2$—, —CH$_2$NHCH$_2$—, —CH$_2$CH$_2$NHCH$_2$—, or —CH$_2$NHCH$_2$CH$_2$—;

R$^3$ is imidazolyl, pyridyl, thiazolyl, pyrrolyl, benzimidazolyl, quinolyl, isoquinolyl or imidazopyridyl, in which lower in reference to alkyl groups refers to such groups having 1 to 6 carbon atoms.

14. A method of claim 13 wherein Ar is 2- or 3-nitrophenyl, 2,3-dichlorophenyl, 2-trifluormethylphenyl, pentafluorophenyl, pyridyl or halopyridyl.

15. A method of claim 13 wherein R is hydrogen, methyl, ethyl, n-propyl, isopropyl, or benzyl.

16. A method of claim 13 wherein R is hydrogen.

17. A method of claim 13 wherein R$^1$ is hydrogen, methyl, ethyl, n-propyl or i-propyl and R$^2$ is methyl or ethyl.

18. A method of claim 13 wherein R$^1$ and R$^2$ are independently methyl or ethyl.

19. A method of claim 13 wherein B is —CH$_2$F, —CHF$_2$, CF$_3$, or —CH$_2$Cl.

20. A method of claim 36 wherein X is —CH$_2$, —CH(CH$_3$)—, —CH(CH$_3$)CH$_2$——CH$_2$CH(CH$_3$)—, —CH$_2$O—, —(CH$_2$)$_2$—O—, —CH$_2$CH$_2$—, —CH$_2$CH$_2$CH$_2$—, —CH$_2$S—, —CH$_2$NH—, —CH$_2$NHCH$_2$—, or —CH$_2$NHCH$_2$CH$_2$—.

21. A method of claim 13 wherein R$^3$ is imidazolyl or pyridyl.

22. A method of claim 13 wherein R$^3$ is 1-imidazolyl or pyridyl-3-yl.

23. A method of claim 13 in which the compound of formula Ia is 2-trifluoromethyl-1,4-dihydro-6-dihydro-6-(imidazol-1-ylmethyl)-4-(3-nitrophenyl)pyridine-3,5-dicarboboxylic acid diethyl ester or a pharmaceutically acceptable salt thereof.

24. A method of claim 13 in which the compound of formula Ia is 2-fluoromethyl-1,4-dihydro-6-(imidazol-1-ylmethyl) -4-(3-nitrophenyl)pyridine-3,5-carboboxylic acid 5-ethyl 3-methyl ester or a pharmaceutically acceptable salt thereof.

25. A method of inhibiting blood platelet aggregation in a mammal in need thereof, comprising administering to such mammal an amount effective to inhibit blood platelet aggregation of a compound of the formula $$\begin{array}{c} \text{Ar} \\ R^1O_2C \diagup\!\!\!\diagdown CO_2R^2 \\ \beta\text{—}\diagup \quad \diagdown \\ \alpha\text{—}\diagup \quad \diagdown X\text{—}R^3 \\ B \quad N \\ \quad | \\ \quad R \end{array} \quad \text{(Ia)}$$

or a pharmaceutically acceptable salt thereof, wherein
α and β together are a bond and additionally, when B is an electron withdrawing group, α is —OH and β is —H;

Ar is phenyl, pyridyl, quinolyl or benzimidazolyl, optionally substituted by one or two substituents independently selected from halogen, lower alkyl, lower alkoxy, haloloweralkyl, haloloweralkoxy, —NO$_2$, —NH$_2$, —CN, loweralkylamino, diloweralkylamino, carboxy, loweralkyloxycarbonyl, acyl of 2 to 7 carbon atoms, or acylamino of 2 to 7 carbon atoms, or pentafluorphenyl;

R is hydrogen, methyl, ethyl, n-propyl, isopropyl or benzyl;

R$^1$ and R$^2$ are independently selected from hydrogen, methyl, ethyl, n-propyl, isopropyl, butyl, methoxymethyl, ethoxymethyl, methoxypropyl, aminoethyl, 2-aminoethyl, 3-aminopropyl, dimethylaminoethyl, 2-carboxyethyl, methoxycarbonylmethyl, ethoxycarbonylethyl, benzyl, 2-phenethyl, pyridylmethyl, pridylethyl, imidazolylmethyl or imidazolylethyl;

B is —CN, —CH$_2$F, —CHF$_2$, CF$_3$, OR —CH$_2$Cl;

X is —NH—, —O—, —S—, —CH₂, —CH(CH₃)—, —CH(CH₃)CH₂—, —CH₂CH(CH₃)—, —OCH₂—, —CH₂O—, —(CH₂)₂—O—, —CH₂CH₂—, —CH₂CH₂CH₂—, —CH₂S, —CH₂SCH₂—, —CH₂CH₂SCH₂—, CH₂SCH₂CH₂—, —CH₂NHCH₂—, —CH₂CH₂NHCH₂—, or —CH₂NHCH₂CH₂—;

R³ is imidazolyl, pyridyl, thiazolyl, pyrrolyl, benzimidazolyl, quinolyl, isoquinolyl or imidazopyridyl, in which lower in reference to alkyl groups refers to such groups having 1 to 6 carbon atoms.

26. A method of claim 25 wherein Ar is 2- or 3-nitrophenyl, 2,3-dichlorophenyl, 2-trifluormethylphenyl, pentafluorophenyl, pyridyl or halopyridyl.

27. A method of claim 25 wherein R is hydrogen, methyl, ethyl, n-propyl, isopropyl, or benzyl.

28. A method of claim 25 wherein R is hydrogen.

29. A method of claim 25 wherein R¹ is hydrogen, methyl, ethyl, n-propyl or i-propyl and R² is methyl or ethyl.

30. A method of claim 25 wherein R¹ and R² are independently methyl or ethyl.

31. A method of claim 25 wherein B is —CH₂F, —CHF₂, CF₃, or —CH₂Cl.

32. A method of claim 28 wherein X is —CH₂, —CH(CH₃)—, —CH(CH₃)CH₂——CH₂CH(CH₃)—, —CH₂O—, —(CH₂)₂—O—, —CH₂CH₂—, —CH₂CH₂CH₂—, —CH₂S—, —CH₂NH—, —CH₂NHCH₂—, or —CH₂NHCH₂CH₂.

33. A method of claim 25 wherein R³ is imidazolyl or pyridyl.

34. A method of claim 25 wherein R³ is 1-imidazolyl or pyridyl-3-yl.

35. A method of claim 25 in which the compound of formula Ia is 2-trifluoromethyl-1,4-dihydro-6-(imidazol-1-ylmethy)-4-(3-nitrophenyl)pyridine-3,5-dicarboboxylic acid diethyl ester or a pharmaceutically acceptable salt thereof.

36. A method of claim 25 in which the compound of formula Ia is 2-fluoromethyl-1,4-dihydro-6-(imidazol-1-ylmethyl)-4-(3-nitrophenyl)pyridine-3,5-carboxylic acid 5-ethyl 3-methyl ester or a pharmaceutically acceptable salt thereof.

* * * * *